US00PP35008P2

(12) United States Plant Patent
Gomez Bullis

(10) Patent No.: US PP35,008 P2
(45) Date of Patent: Feb. 28, 2023

(54) ***NEOREGELIA* PLANT NAMED 'FREYA'**

(50) Latin Name: ***Neoregelia carolinae* X (*Neoregelia hybrida* 'Luxurians' X *Neoregelia hybrida* 'Passion')**
Varietal Denomination: Freya

(71) Applicant: BULLIS BROMELIADS INC., Princeton, FL (US)

(72) Inventor: Patricia E. Gomez Bullis, Princeton, FL (US)

(73) Assignee: BULLIS BROMELIADS, Princeton, FL (US)

( * ) Notice: Subject to any disclaimer, the term of this patent is extended or adjusted under 35 U.S.C. 154(b) by 0 days.

(21) Appl. No.: 17/857,128

(22) Filed: Jul. 4, 2022

(51) Int. Cl.
*A01H 5/02* (2018.01)
*A01H 6/22* (2018.01)
*A01H 5/12* (2018.01)

(52) U.S. Cl.
USPC ..... Plt./370
CPC ..... *A01H 6/22* (2018.05); *A01H 5/12* (2013.01)

(58) Field of Classification Search
USPC ..... Plt./370
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Neoregelia* plant named 'Freya', characterized by its broad and outwardly arching growth habit; relatively broad leaves that are outwardly arching and recurved; glossy leaves that are greyed yellow in color with distinct medium and dark green-colored longitudinal stripes, dark green-colored margins and deep red-colored apices; upper (younger) leaves are mostly deep red in color; flower development is not required for red color development; and good interiorscape and landscape performance.

1 Drawing Sheet

Botanical designation: *Neoregelia carolinae* X (*Neoregelia hybrida* 'Luxurians' X *Neoregelia hybrida* 'Passion').
Cultivar denomination: 'FREYA'.

BACKGROUND OF THE INVENTION

The present invention relates to a new and distinct cultivar of *Neoregelia* plant, botanically known as *Neoregelia carolinae* X (*Neoregelia hybrida* 'Luxurians' X *Neoregelia hybrida* 'Passion'), and hereinafter referred to by the name 'Freya'.

The new *Neoregelia* plant is a product of a planned breeding program conducted by the Inventor in Princeton, Fla. The objective of the breeding program is to create new *Neoregelia* plants with uniquely colored leaves.

The new *Neoregelia* plant originated from a cross-pollination made by the Inventor in 2009 in Princeton, Fla. of an unnamed proprietary selection of *Neoregelia carolinae*, not patented, as the female, or seed, parent with an unnamed proprietary selection of *Neoregelia hybrida* 'Luxurians' X *Neoregelia hybrida* 'Passion ', not patented, as the male, or pollen, parent. The new *Neoregelia* plant was discovered and selected by the Inventor as a single plant within the progeny of the stated cross-pollination in a controlled greenhouse environment in Princeton, Fla. in 2009.

Asexual reproduction of the new *Neoregelia* plant by offsets in a controlled environment in Princeton, Fla. since 2010, has shown that the unique features of this new *Neoregelia* plant are stable and reproduced true to type in successive generations.

SUMMARY OF THE INVENTION

Plants of the new *Neoregelia* have not been observed under all possible combinations of environmental conditions and cultural practices. The phenotype may vary somewhat with variations in environment conditions such as temperature and light intensity without, however, any variance in genotype.

The following traits have been repeatedly observed and are determined to be the unique characteristics of 'Freya'. These characteristics in combination distinguish 'Freya' as a new and distinct *Neoregelia* plant:

1. Broad and outwardly arching growth habit.
2. Relatively broad leaves that are outwardly arching and recurved.
3. Glossy leaves that are greyed yellow in color with distinct medium and dark green-colored longitudinal stripes, dark green-colored margins and deep red-colored apices; upper (younger) leaves are mostly deep red in color; flower development is not required for red color development.
4. Good interiorscape and landscape performance.

Plants of the new *Neoregelia* differ primarily from plants of the female parent selection in the following characteristics:

1. Leaves of plants of the new *Neoregelia* are broader than leaves of plants of the female parent selection.
2. Leaves of plants of the new *Neoregelia* develop red coloration earlier than leaves of plants of the female parent selection.
3. Leaves of plants of the new *Neoregelia* are more durable and resistant to abrasions and physical damage than leaves of plants of the female parent selection.

Plants of the new *Neoregelia* differ primarily from plants of the male parent selection in the following characteristics:

1. Plants of the new *Neoregelia* are finish in about eleven months whereas plants of the male parent selection finish in about 18 months.
2. Plants of the new *Neoregelia* and the male parent selection differ in leaf color as plants of the new *Neoregelia* are greyed yellow in color with distinct medium and dark green-colored longitudinal stripes, dark green-colored margins and deep red-colored apices whereas leaves of plants of the male parent selection are solid green in color.

Plants of the new *Neoregelia* can be compared to plants of the *Neoregelia carolinae* X (*Neoregelia macrosepala* X *Neoregelia meyendorfii*) 'Dharma', disclosed in U.S. Plant Pat. No. 33,279. In side-by-side comparisons, plants of the new *Neoregelia* and 'Dharma' differ primarily in the leaf color as this new *Neoregelia* and 'Dharma' differ in leaf color as leaves of plants of the new *Neoregelia* are greyed yellow in color with distinct medium and dark green-colored longitudinal stripes, dark green-colored margins and deep red-colored apices whereas leaves of plants of 'Dharma' are dark green in color with distinct light yellow green-colored stripes and margins and red purple-colored apices.

BRIEF DESCRIPTION OF THE PHOTOGRAPH

The accompanying colored photograph illustrates the overall appearance of the new *Neoregelia* plant showing the colors as true as it is reasonably possible to obtain in colored reproductions of this type. Colors in the photograph may differ slightly from the color values cited in the detailed botanical description which accurately describe the colors of the new *Neoregelia* plant. The photograph is a top perspective view of a typical flowering plant of 'Freya' grown in a container.

DETAILED BOTANICAL DESCRIPTION

The aforementioned photograph and following observations, measurements and values describe flowering plants grown during the spring in 15-cm containers in a polypropylene-covered greenhouse in Princeton, Fla. and under cultural practices typical of commercial *Neoregelia* production. During the production of the plants, day temperatures ranged from 28° C. to 30° C., night temperatures ranged from 18° C. to 22° C. and light levels averaged 2,500 foot-candles. Plants were twelve months old when the photograph and description were taken. In the following description, color references are made to The Royal Horticultural Society Colour Chart, 2015 Edition, except where general terms of ordinary dictionary significance are used.

Botanical classification: *Neoregelia carolinae* X (*Neoregelia hybrida* 'Luxurians' X *Neoregelia hybrida* 'Passion') 'Freya'.

Parentage:

*Female, or seed, parent*.—Unnamed proprietary selection of *Neoregelia carolinae*, not patented.

*Male, or pollen, parent*.—Unnamed proprietary selection of *Neoregelia hybrida* 'Luxurians' X *Neoregelia hybrida* 'Passion', not patented.

Propagation:

*Type*.—By offsets.

*Time to initiate roots, summer*.—About 30 days at ambient temperatures about 28° C. to 30° C.

*Time to initiate roots, winter*.—About 40 days at ambient temperatures about 28° C. to 30° C.

*Time to produce a rooted young plant, summer*.—About three months at ambient temperatures about 28° C. to 30° C.

*Time to produce a rooted young plant, winter*.—About four months at ambient temperatures about 18° C. to 22° C.

*Root description*.—Medium in thickness, fibrous; typically yellowish beige to light brown in color, actual color of the roots is dependent on substrate composition, water quality, fertilizer type and formulation, substrate temperature and physiological age of roots.

*Rooting habit*.—Moderately freely branching; medium density.

Plant description:

*Plant and growth habit*.—Broad and outwardly arching growth habit; leaves in rosettes; plants readily produce uniform offsets; vigorous growth habit.

*Plant height*.—About 13 cm.

*Plant diameter or spread*.—About 44.5 cm.

*Internode length*.—About 2 mm.

*Stem diameter at the soil level*.—About 3.75 cm.

*Stem texture*.—Smooth, glabrous.

*Stem color*.—Close to NN155A.

Leaf description:

*Arrangement*.—Rosette, spiral phyllotaxis; simple; sessile, clasping.

*Shape*.—Broadly oblong with broader sheathing base.

*Apex*.—Cuspidate to short aristate.

*Base*.—Truncate, clasping.

*Margin*.—Serrate, spinose.

*Length*.—About 27.5 cm.

*Width, mid-section*.—About 7.5 cm.

*Width, widest part towards the base, flattened*.—About 9.75 cm.

*Texture and luster, upper and lower surfaces*.—Smooth, glabrous; leathery; narrowly and longitudinally ribbed; glossy, shiny.

*Venation pattern*.—Parallel.

*Color*.—Upper (younger) leaves, upper surface: Distally, close to 53A and proximally, close to N155B; venation, similar to lamina colors. Upper (younger) leaves, lower surface: Distally, close to 58A and proximally, close to N155B; venation, similar to lamina colors. Lower (older) leaves, upper surface: Centers: Close to 160B and 160C. Longitudinal stripes: Close to 146A, 147A and NN137A. Margins: Close to 147A and NN137A. Towards the apex: Close to 53A; younger leaves have more red coloration than older leaves; oldest leaves may have little to no red coloration. Towards the base: Close to 160D, slightly and variably tinged with close to 148B. Venation: Similar to lamina colors. Lower (older) leaves, lower surface: Centers: Close to 160C and 160D. Longitudinal stripes: Close to 146A, 147A and NN137A. Margins: Close to 146A, 147A and NN137A. Towards the apex: Close to 58A; younger leaves have more red coloration than older leaves; oldest leaves may have little to no red coloration. Towards the base: Close to 160C and 160D slightly and variably tinged with close to 148B. Venation: Similar to lamina colors.

Inflorescence description:

*Inflorescence form*.—Terminal flat-topped compact corymb located inside the leaf rosette; about 84 flowers develop per inflorescence.

*Time to flower*.—Plants begin flowering about 60 to 70 days after planting; plants flower naturally during the spring in Florida.

*Flower longevity*.—Dependent on temperature, individual flowers last about four to six days on the plant; flowers persistent.

*Fragrance*.—None detected.

*Inflorescence height*.—About 5.5 cm.

*Inflorescence diameter*.—About 3.5 cm.

*Flower size*.—Length: About 4.5 cm. Diameter: About 7 mm.

*Petals*.—Quantity per flower: Three in a single whorl; lower 75% of the petals are fused. Shape, free part: Lanceolate. Apex: Sharply acuminate. Margin: Entire. Length: About 2.5 cm. Width at base of free part: About 4 mm. Texture and luster, upper and lower surfaces: Smooth, glabrous; slightly glossy. Color: When opening and fully opened, upper (inner) surface: Distally, close to 94C and proximally, close to NN155D. When opening and fully opened, lower (outer) surface: Distally, close to 94B and proximally, close to NN155D.

*Flower bracts*.—Quantity per flower: One. Shape: Narrowly lanceolate. Apex: Acute. Base: Truncate. Length: About 3 cm. Width: About 7.5 mm. Texture and luster, upper and lower surfaces: Membranous and translucent; slightly glossy. Color, upper and lower surfaces: Close to 157A to 157B.

*Sepals*.—Quantity per flower: Three in a single whorl; lower 50% of the sepals are fused. Shape: Narrowly lanceolate. Apex: Acuminate. Length: About 3 cm. Width: About 3 mm. Texture and luster, upper and lower surfaces: Smooth, glabrous; moderately glossy. Color, upper and lower surfaces: Free part, close to 144A and fused part, close to NN155A.

*Peduncles*.—Length: About 3 cm. Diameter: About 1.5 cm. Strength: Strong, sturdy. Aspect: Typically erect. Texture and luster: Smooth, glabrous; glossy. Color: Close to NN155A.

*Pedicels*.—Length: About 1 cm. Diameter: About 2 mm by 5 mm. Strength: Strong, flexible. Aspect: Depending on position in the inflorescence, typically erect to outwardly and curving upright. Texture and luster: Smooth, glabrous; glossy. Color: Close to 155A.

*Stamens*.—Quantity per flower: Six. Filament length: About 1 cm; partially adnate to the petals. Filament color: Close to NN155D. Anther shape: Lanceolate. Anther length: About 2.25 mm. Anther color: Close to 158C. Pollen amount: None observed.

*Pistils*.—Quantity per flower: One. Pistil length: About 1.75 cm. Stigma shape: Elongated oblong. Stigma color: Close to 157C. Style length: About 1.25 cm. Style color: Close to NN155D. Ovary color: Close to 155A to 155B.

*Fruits and seeds*.—To date, fruit and seed production have not been observed on plants of the new *Neoregelia*.

Interior & garden performance: Plants of the new *Neoregelia* have been observed to have good postproduction longevity under interior conditions, to have good garden performance and to tolerate temperatures ranging from 2° C. to 37° C.

Pathogen & pest tolerance: Plants of the new *Neoregelia* are relatively tolerant to *Pythium* (*Pythium* spp.) and *Phytophtora* (*Phytophtora cinnamoni*). To date, tolerance to pests and other pathogens common to *Neoregelia* plants has not been observed.

It is claimed:

1. A new and distinct *Neoregelia* plant named 'Freya' as illustrated and described.

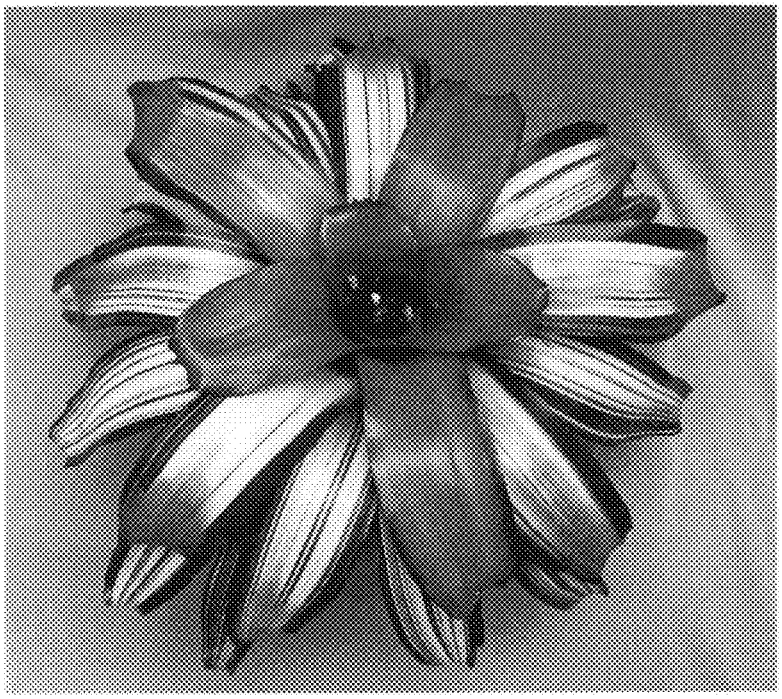

* * * * *